United States Patent

Marasco, Jr.

[11] Patent Number: 6,083,209
[45] Date of Patent: *Jul. 4, 2000

[54] TISSUE DEBRIDING APPARATUS

[76] Inventor: Patrick V Marasco, Jr., 36 Towne Rd., Boxford, Mass. 01921

[ * ] Notice: This patent is subject to a terminal disclaimer.

[21] Appl. No.: 09/156,115

[22] Filed: Sep. 18, 1998

Related U.S. Application Data

[62] Division of application No. 08/682,888, Jul. 11, 1996, Pat. No. 5,848,998.

[51] Int. Cl.⁷ .................................................. A61M 35/00
[52] U.S. Cl. ............................................................ 604/290
[58] Field of Search ............................ 604/23, 289–294, 604/319, 356, 408; 128/202.12, DIG. 24; 606/131

[56] References Cited

U.S. PATENT DOCUMENTS

| | | | |
|---|---|---|---|
| 3,744,491 | 7/1973 | Fischer . | |
| 4,224,941 | 9/1980 | Stivala | 128/207.26 |
| 4,236,513 | 12/1980 | LoPiano | 128/184 |
| 4,772,259 | 9/1988 | Frech et al. | 604/23 |
| 5,149,331 | 9/1992 | Ferdman et al. | 604/290 |
| 5,312,385 | 5/1994 | Greco | 604/289 |
| 5,848,998 | 12/1998 | Marasco, Jr. | 604/290 |

Primary Examiner—Ronald Stright
Assistant Examiner—David J. Cho
Attorney, Agent, or Firm—Don Halgren

[57] ABSTRACT

The present invention comprises a wound treatment apparatus including a flexible transparent envelope of generally elongated configuration having a first end and a second end, a primary opening at the first end of the envelope, the primary opening having a peripheral margin therearound, the margin including a securement band for securement of the flexible envelope to a portion of the body being treated. The apparatus includes a first access port through the envelope, a wound fluid applying gun having an elongated barrel juxtaposable in a close fitting relationship to the first access port, to supply a pressurized wound treatment fluid onto any body portion attached to the envelope, and a drain port in communication with a collection chamber for draining any effluent fluid, tissue and/or gas from that envelope.

2 Claims, 4 Drawing Sheets

TISSUE DEBRIDING APPARATUS

This is a Divisional Application of U.S. patent application Ser. No. 08/682,888, filed Jul. 11, 1996, now U.S. Pat. No. 5,848,998, issued Dec. 15, 1998.

BACKGROUND OF THE INVENTION

1. Field of the Invention

This invention relates to apparatus for washing and debriding tissue at various wound sites on the human body.

2. Prior Art

Wound management is a significant portion of all medical practice today. Wounds typically occur from a burn, a contaminated trauma (blunt trauma), chronic ulceration, tendon laceration, abscess cavity to be drained, cellulitus (skin irritation), open bone fracture (compound fracture), and pressure sores. Such wounds and their treatment constitute a large percentage of the treatment provided to medical patients. The number of methods for wound cleansing and debridement have been developed over the past years. Those methods have included wound cleansers such as povidone-iodine, hydrogen-peroxide, acetic acid, and chlorinated solutions which however, have cytotoxic effect on cells. Other types of wound cleaning and debridement include piston-type syringe irrigation, whirlpool treatments, wet to dry saline gauze dressings, surgical/mechanical debridement, enzymatic debridement, absorbent dextranomor microbeads, and pulsed lavage.

Syringe irrigation is sufficient for cleaning most simple wounds. Large complicated wounds, however, require large quantities of irrigant for effective cleansing and debridement. Whirlpool treatments are often utilized for cleansing larger wounds and appear to be common in physical therapy departments. However, with certain deep wounds flushing and debridement is difficult to achieve. The patient must often be uncomfortably positioned in order to direct jets at the wound. If a patient is incontinent, or if multiple wounds are present, cross contamination between those multiple wounds may occur. Wet to dry saline gauze dressings are simple to use and are inexpensive for the patient, but in removal of that dressing they may also damage healthy tissue and may be painful. Such dressing changes may also be a labor intensive procedure.

A relatively new procedure in wound management includes pulsed lavage wherein a pulsating water jet is directed toward the wound site, which method is fairly effective in removing debris and bacteria from those wounds.

Pulse lavage irrigation devices typically utilize a cone shaped shield, having an open base which is placed over the wound. The shield is utilized to minimize splashing to protect the health care worker and to prevent aerosolization of body fluid. Typically a pan would be held against a lower portion of the skin of a patient being treated. A suction tube may be hung into the pan so as to drain out fluid. The fluid is typically saline or saline with an antibiotic added for wound debridement and sterilization.

A number of such physical devices are shown in the prior art to isolate and permit treatment of certain wound sites. One such device is shown in U.S. Pat. No. 5,447,504 to Baker at el. showing a misting apparatus which comprises a container secured to a limb of a patient at each end, by a rigid cuff. The cuff is held onto the limb by a securement strap and each cuff has an opening to permit an elongated listing tool to be fixedly arranged thereto. This apparatus may be satisfactory for applying a mist to a limb, for the prevention of that limb from drying out, but it has rigid conduits which puts limitations on the manipulability of the device which prevents it from applying a wide range of debriding and cleansing actions. U.S. Pat. No. 3,867,929 to Joyner et el. shows an ultrasonic treatment device in which an acoustically transparent container is wrapped around the limb containing a wound site. The container has ultrasonic transducers spaced therearound for generating acoustic vibrations through a fluid within the container and onto the wound site. This, however does not provide the flushing necessary of many wound examples.

A further means for treating surface wounds is shown in U.S. Pat. No. 3,288,140 to McCarthy. This device includes cup like housings which are placed against the wound site to permit containment of the spray from a nozzle and drainage therefrom as well.

Other interesting limb treatment devices are shown in U.S. Pat. No. 3,094,983 to Macleod, U.S. Pat. No. 2,113,253 to Gray, and U.S. Pat. No. 1,105,365 to McQuhae, each showing an unusual containment for a limb to permit bathing or improve blood circulation therewithin. Each of these devices, however are unduly complicated and are not conducive to efficient personalized and adaptive treatment either at home or in the field on the wound of a patient. The prior art requires that the patients wound's conform to the apparatus, and not vice-versa.

It is thus an object of the present invention, to overcome the shortcomings of the prior art.

It is a further object of the present invention to permit a wound treatment apparatus which may be utilized in a medical facility, in a home, or in a field environment to a broad array of wound sites, readily adaptable to each kind, which apparatus also protects the worker as well as the patient being treated.

It is yet a further object of the present invention, to provide a wound treatment apparatus which prevents cross contamination of a wound site from outside the environment or from other wound sites on that patient, and minimizes the likelihood of contamination from that patient to a further patient.

BRIEF SUMMARY OF THE INVENTION

The present invention comprises an apparatus for the washing and debridement of wounds on limbs and body portions of patients. Such apparatus may be utilized outside of a formal medical facility, and for use in a place such as the home or in the field. It is the intent of this invention to replace or minimize the use of a whirlpool bath, to eliminate cross-contamination of body fluids, and to minimize the spread of bacteria, hepatitis and other staff and pathogenic organisms.

The present invention comprises a flexible envelope of transparent plastic material having a first primary opening for receipt of a body limb or for attachment to a body portion having a wound site thereon. The envelope will include at least one secondary opening having a flexible support collar therearound for insertion of a fluid delivery device. The fluid delivery device may comprise a hand manipulable gun for the delivery of fluid under pressure. The fluid may be a gas and/or fluid mixture. The gas proposed may comprise oxygen or carbon dioxide or hydrogen peroxide useful for sterilization purposes. The flexible envelope covering the wound should contain at least one tertiary port for the drainage and withdrawal of fluid, washed away tissue, and for the release of pressurized gas which has been delivered into the envelope.

In a first preferred embodiment of the present invention, the flexible transparent envelope comprises a bag-like structure having an enlarged central portion with a tapered narrowed end with an opening thereat. An elasticized self-sealable or securable strap or band is disposed adjacent to periphery of the opening at the narrow end. This permits the distal end of an arm or foot to be inserted within the bag for debridement of a wound therein. The invention includes a pressurized source of fluid which fluid may be a saline solution and a gas such as carbon dioxide or oxygen or the like, supplied by a hand manipulable pressurized gun, the gun fitting in the access port in a snug fitting relation, the access port having the collar which collar may be stretchably elasticized, meeting with the chamber of the gun so as to minimize or eliminate any loss of pressure or fluid from within the envelope. The containment envelope may have a drainage port disposed through the envelope at a position generally diametrically opposed to the access port therein. The drainage port has a conduit which is in fluid communication with a disposable collection bag or a suction line.

In a further preferred embodiment of the present invention, the apparatus includes a flexible envelope of bag-like shape, having a primary opening therethrough. The primary opening has annular or peripheral lip with a mildly aggressive adhesive disposed thereabout. The adhesive may have a cover strip thereon, removable upon the need to secure the envelope about a wound site. An access port is preferably disposed at an uppermost end of the envelope, the access port having a flexible collar which permits the receipt of the hand held manipulable pressurized gun for the delivery of fluid and/or gas at a pressure, onto the wound of a patient's body anywhere within the envelope. A drainage port is disposed adjacent the annular periphery of the opening of the envelope. The drainage port has a flexible collar which is attached to a flexible line in fluid communication with a disposable collection bag or suction sump. The envelope and debridement apparatus of the present embodiment is particularly adaptable towards portions of a body torso or the like, having a wound site thereon which is not conducive to complete enclosure within the envelope itself, but having the envelope only adjacent to and disposed thereabout.

In yet a still further preferred embodiment of the present invention includes a large flexible envelope capable of enclosing the entire body of a patient from the neck portion downwardly. The envelope may comprise a bag-like structure having an opening at one end, with a flexible collar-like structure thereat and a sealable strap therearound, and/or a longitudinally directed zipper running the longitudinal length of the bag from the opening at one (neck) end thereof to the lower or distal end of the bag. The envelope in this preferred embodiment includes a plurality of uppermost access ports disposed in a linear array along the uppermost longitudinal portion of the envelope. Each spaced apart access port may have slit like openings thereacross, so as to be functionally sealed under moderate gas treatment pressure supplied by the hand manipulable fluid gun and/or gas or other gas pressure treatment source, the fluid gun source being hand manipulably-directable toward a patient's particular wound site(s) within the bag at the spaced apart locations. This embodiment includes a plurality of drainage ports spaced longitudinally apart and preferably diametrically opposite the access ports in the envelope. The drainage ports are, as in the aforementioned embodiments, attached to flexible conduits which drain into a disposable collection bag or a suction system, to permit withdrawal and containment of the tissue particles, debridement washed from the patient, and pressurized gas within the envelope. A distal dryer port may be disposed at the end of the envelope opposed to the neck attachment end thereof. The dryer port would permit a further transfer of gas (treated/heated with or without medicaments) to or out of the envelope in which the patient was situated. The gas may be fed into the envelope to maintain it away from contact with the patient's skin/wound, except of course, at the primary opening of the envelope, where the envelope is in a sealing relationship with the patient's skin.

It is contemplated that medicaments may be included within the pressurized fluid projected onto a wound site. Such medicaments may include clotting factor material such as topical thrombin utilized to treat burns and the like which would be directed towards such wound site either in a pulse or a study irrigation treatment.

In yet a further embodiment contemplated by the present invention, such an envelope with a securement collar therearound may be utilized for bathing animals or for the treatment of animals or patients with a particular skin problem. The access port may be utilized to deliver under pressure a fluid cleaning and hot or cool air at a pressure, to maintain the bag away from the body and wound sites within the envelope, and that envelope may have one or more drainage ports at its lowermost portion and a feed port for supply of hot or warm air from a blower or dryer to dry off the patient and to heat or cool it. A gas release valve may be arranged in the wall of the envelope, to release gas at a pre-determined pressure, to prevent excess pressure from building-up within the envelope. Treatment includes pressurizing the atmosphere within the envelope, so as to apply pressure without contact, at a wound site or patient's organ within the envelope, to help control bleeding, tissue movement, healing or the like.

BRIEF DESCRIPTION OF THE DRAWINGS

The objects and advantages of the present invention will become more apparent, when viewed in conjunction with the following drawings in which.

DESCRIPTION OF THE PREFERRED EMBODIMENTS

Figure 1:
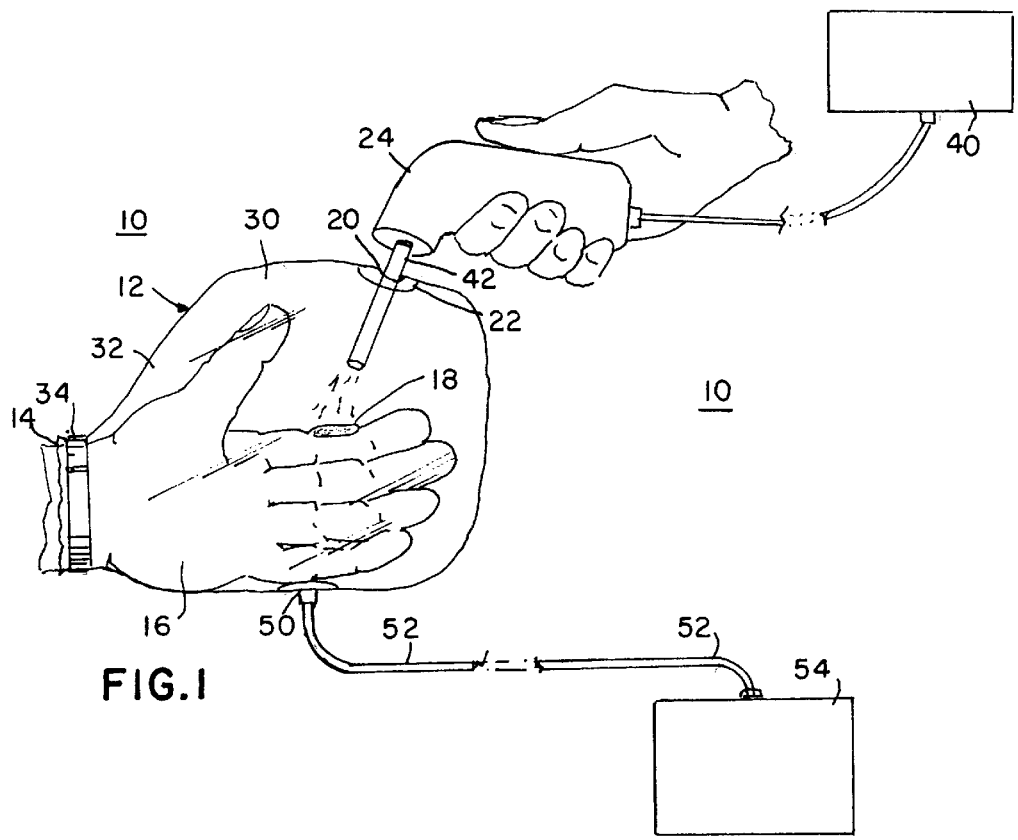
FIG. 1 is a side elevational view of a wound treatment shield and container constructed according to the principles of the present invention, shown utilized on a body part end wound.
Figure 2:
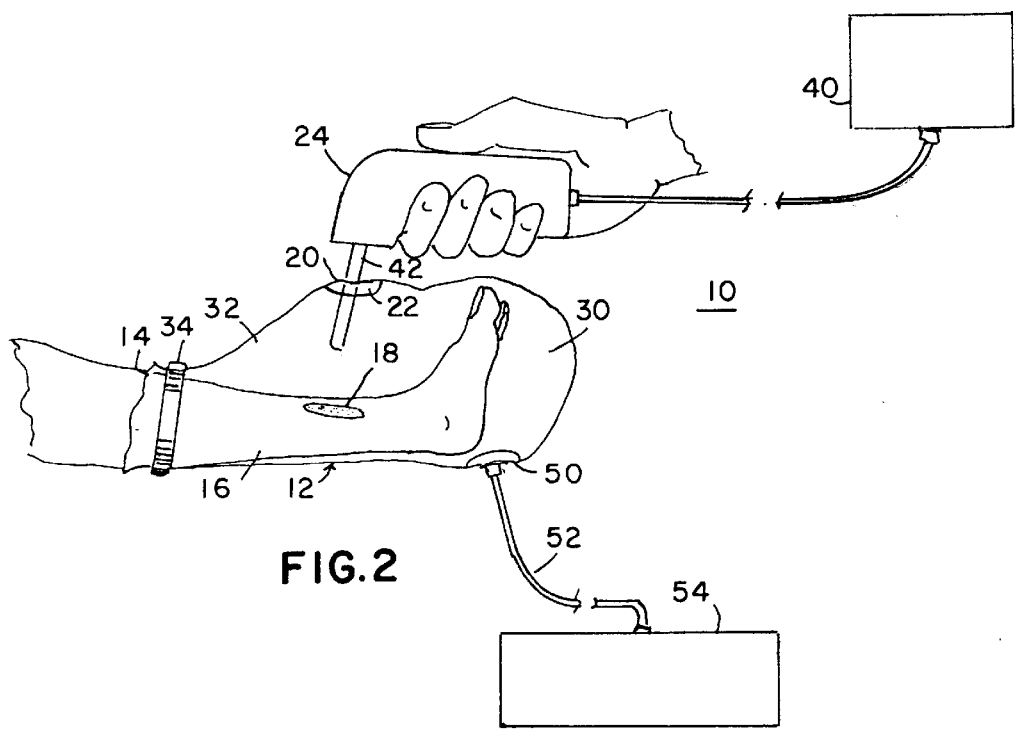
FIG. 2 is a side elevational view of the wound treatment shield container of the present invention, with an envelope arranged around the foot of a patient.

The present invention comprises an apparatus 10 for the washing and debridement of wounds on limbs and body portions of patients, as may be seen in FIGS. 1, 2 et seq. Such apparatus may be utilized outside of a formal medical facility, and for use in a place such as the home or in the field. It is the intent of this invention to replace or minimize the use of a whirlpool bath, to eliminate cross-contamination of body fluids, and to minimize the spread of bacteria, hepatitis and other staff and pathogenic organisms, by a device which can treat a variety of wound site(s) because of its adaptability.

The present invention comprises a flexible envelope 12 preferably comprised of transparent polymeric plastic material having a first primary opening 14 for receipt of a body limb 16 or for attachment to a body portion having a wound site 18 thereon. The envelope 12 will include at least one secondary opening 20, the opening 20 having a flexible reinforced support collar 22 therearound for insertion of a barrel of a fluid delivery device 24. The fluid delivery device may comprise a hand manipulable gun with its own pressure pump therein, not shown, or for the delivery of fluid under pressure, from a pressure or gravity powered source. The fluid may be a gas and/or fluid mixture. The gas proposed may comprise oxygen or carbon dioxide or hydrogen peroxide useful for sterilization purposes. The flexible envelope 12 covering the wound 18 should contain at least one tertiary port 26 for the drainage and withdrawal of fluid, washed-away tissue, and pressurized gas which has been delivered into the envelope 12.

In a first preferred embodiment of the present invention, as shown in FIGS. 1 and 2, the flexible transparent envelope 12 comprises a bag-like structure having an enlarged central portion 30 with a tapered narrowed flexible end 32 with the primary opening 14 thereat. An self-sealable flexible securable strap or band 34, which may be elasticized, is disposed adjacent to periphery of the primary opening 14 at the narrow end of the envelope 12. This permits the distal end of an arm or foot of any dimension/diameter, to be inserted within the bag for debridement of a wound therein. The invention includes a pressurized or gravity fed source of fluid 40, which fluid may be a saline solution and a gas such as carbon dioxide or oxygen or the like, supplied by a hand manipulable delivery device or pressurized gun 24, the barrel of the gun 24 fitting in the access port 20 in a snug fitting relation, the collar 22 meeting with the barrel 42 of the gun 24 so as to minimize or eliminate any loss of pressure or fluid from within the envelope 12. The containment envelope 12 may have a drainage port 50 disposed through the envelope 12 at a position generally diametrically opposed with respect to the access port 20 therein. The drainage port 50 may have a conduit 52 which is in fluid communication with a disposable collection bag 54 or a suction line.

Figure 3:
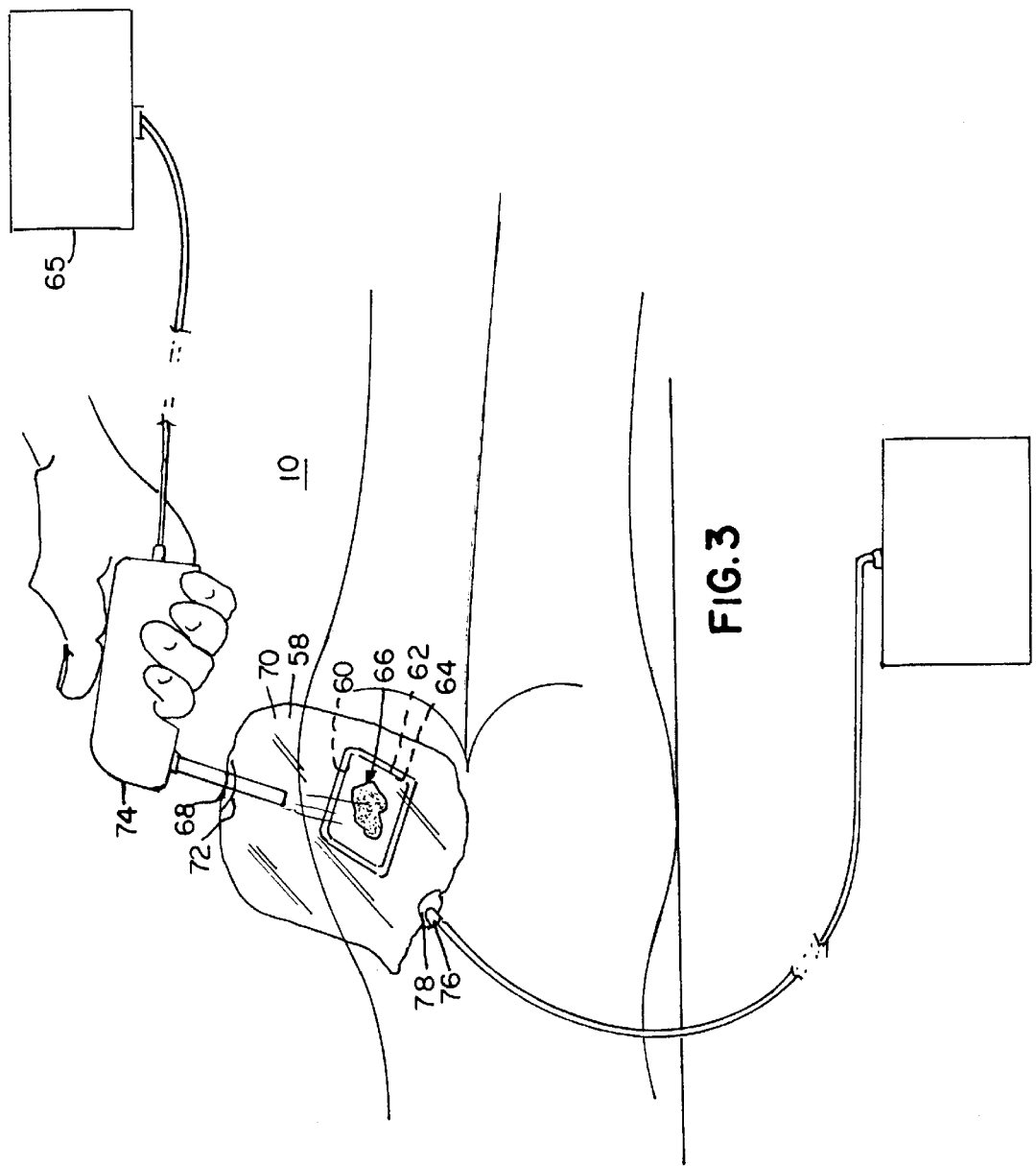
FIG. 3 is a side elevational view of a wound treatment shield and container apparatus of the present invention utilized on the torso portion of a patient.

In a further preferred embodiment of the present invention, as may be seen in FIG. 3, the apparatus 10 includes a flexible envelope 58 of bag-like shape, having a primary opening 60 therethrough. The primary opening 60 has a flexible annular or peripheral lip 62 with a band of mildly aggressive adhesive 64 disposed thereabout. The adhesive 64 may have a cover strip, not shown, thereon, removable upon the need to secure the envelope 58 about a wound site 66. An access port 68 is preferably disposed at an uppermost end 78 of the envelope 58, the access port 68 having a flexible reinforced collar 72 which permits the snug receipt of the delivery barrel of the hand held manipulable pressurized gun 74 for the delivery of fluid and/or gas from a pressure source 65, onto the wound 66 within the envelope 58. A drainage port 76 is disposed adjacent the annular periphery of the primary opening 60 of the envelope 58. The drainage port 76 has a flexible reinforced collar 78 to permit the envelope 58 to be safely manipulated without ripping and allow the port to be held/pulled into a "lowermost" sump-like orientation, the port 76 attached to a flexible line 80 in fluid communication with a disposable collection bag 82 or suction sump. The envelope 58 and debridement apparatus 74 of the present embodiment is particularly adaptable towards portions of a body torso or the like, having a wound site thereon which is not conducive to complete enclosure within the envelope itself, as in the aforementioned embodiments, but having the envelope 58 only "adjacent to" and disposed about the wound site, in a non-body part enclosing manner.

Figure 4:
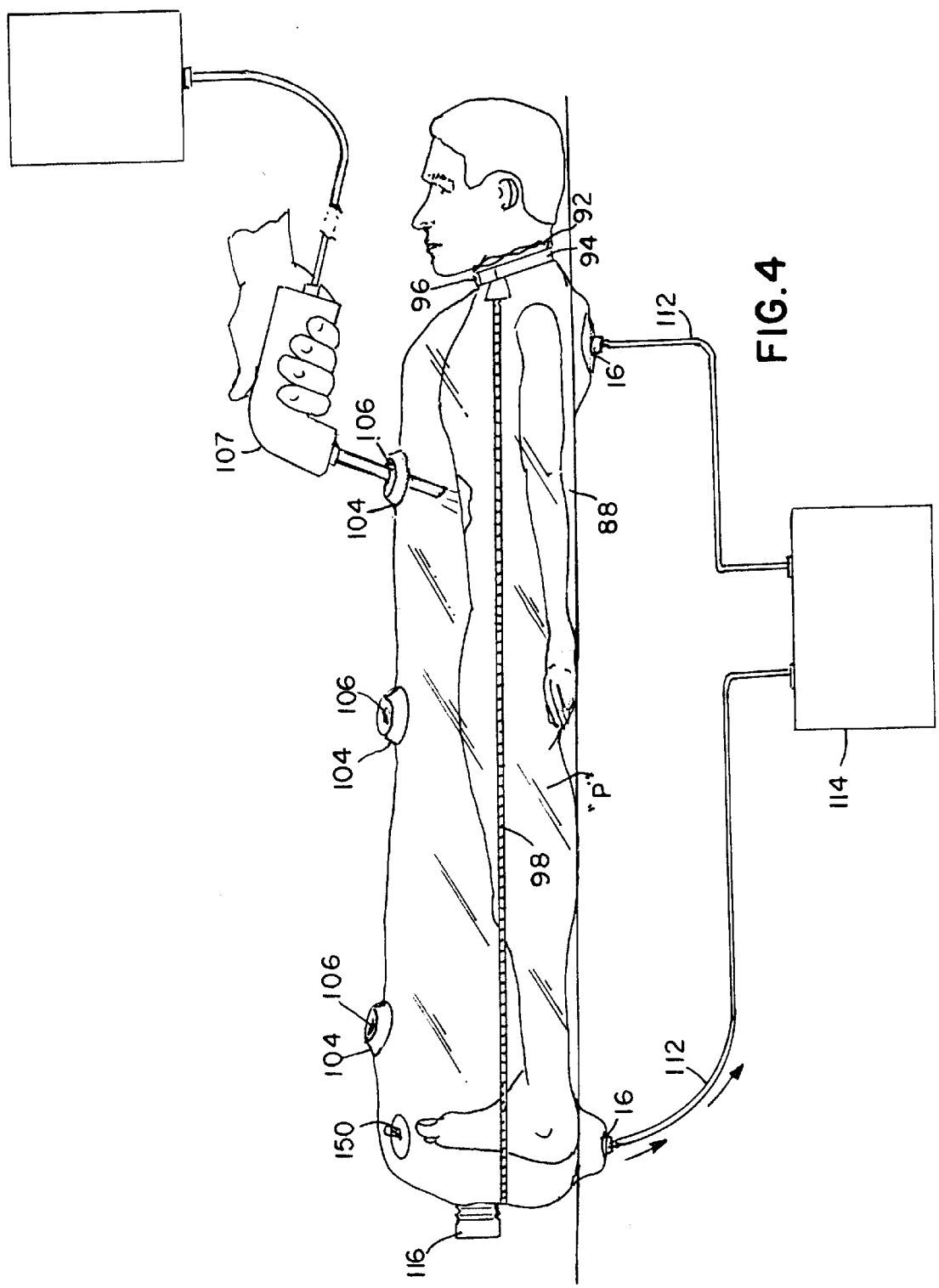
FIG. 4 is a side elevational view of a wound treatment shield container envelope utilized for a near total body enclosure apparatus.

In yet a still further preferred embodiment of the present invention, as shown in FIG. 4, there is disclosed a large flexible envelope 88 capable of enclosing the entire body of a patient from the neck portion downwardly. The envelope 88 may comprise a bag-like structure having a primary opening 90 at a head end 92, with a flexible collar 94 thereat and a sealable strap 96 therearound, and/or a longitudinally directed zipper 98 running the longitudinal length of the envelope 88 from the primary opening 90 at the neck end 92 thereof to the foot or distal end 100 of the envelope 88. The envelope 88 in this preferred embodiment includes a plurality of uppermost access ports 104 disposed in a linear array along the uppermost longitudinal portion of the envelope 88, as shown in FIG. 4. Each spaced apart access port 104 may have an overlapping slit like opening 106 thereacross, so as to be functionally sealed under a certain pre-selected low pressure supplied by a hand manipulable fluid and/or gas delivery gun 107, which gun 107 is hand held so as to be pressurizably directed toward a patient "P", within the envelope 88, the ports 104 being arranged at those spaced apart locations. This embodiment includes a plurality of drainage ports 110 spaced longitudinally apart and diametrically opposite the access ports 104 in the body enclosing envelope 88. The drainage ports 110 are, as in the aforementioned embodiments, each attached to flexible conduits 112 which drain into a disposable collection bag 114 or a suction system, to permit withdrawal and containment of the tissue particles and debridement washed from the patient "P" within the body enclosing envelope 88. A distal dryer port 116 may be disposed at the "foot" end of the envelope 88 as opposed to the neck attachment end 92 thereof. The dryer port 116 would permit a further transfer of gas into or out of the envelope 88 in which the patient "P" was situated.

Figure 5:
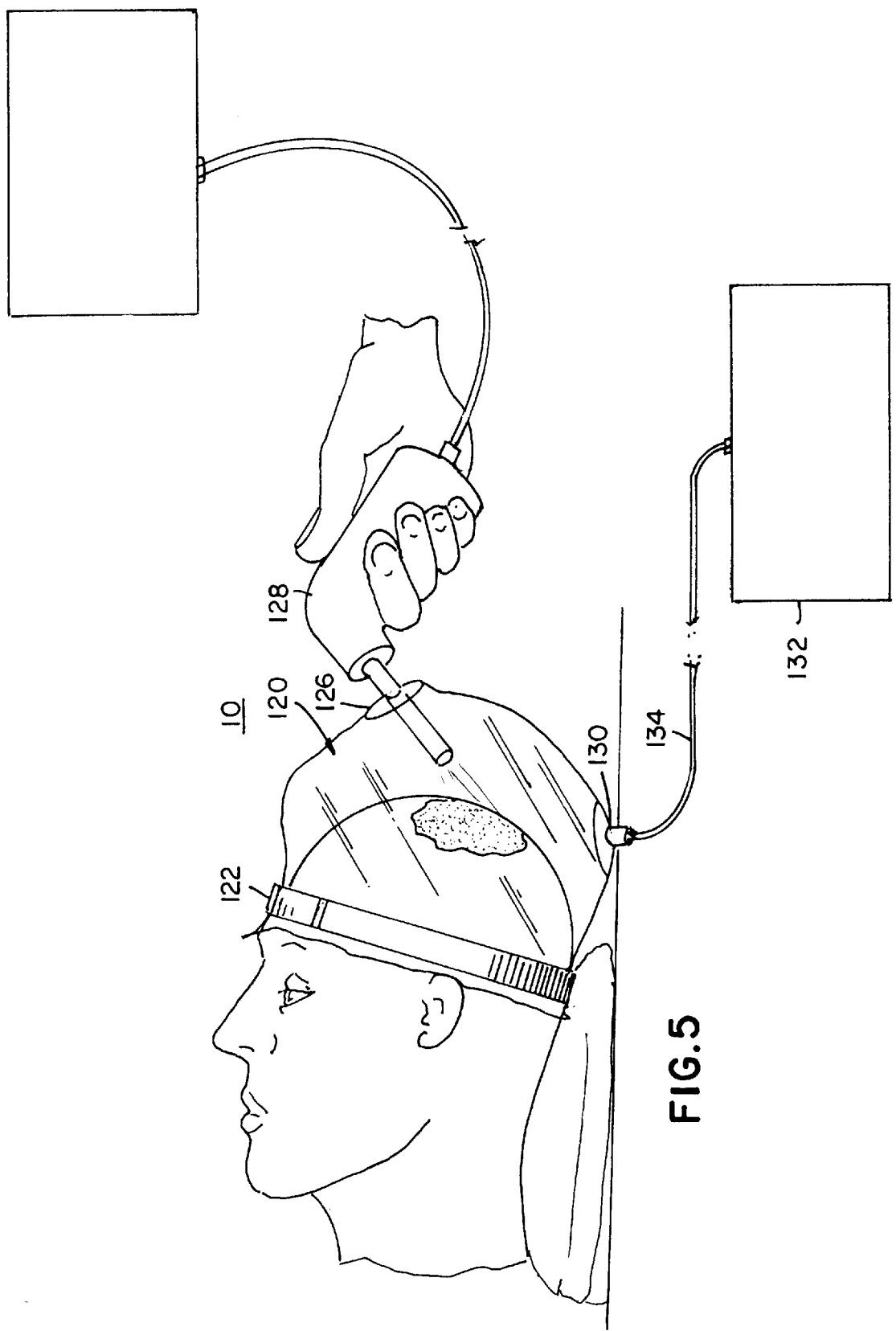
FIG. 5 is a side elevational view of a wound treatment shield container arrangement which may be utilized on the head of a patient having a wound thereon.

A further embodiment of the apparatus is shown in FIG. 5, wherein an envelope 120 of shorter length, of about 12", is arranged onto a patient's head and held there by a securement strap 122. The envelope 120 has an access port 126 for snug entry of a hand held manipulable pressurized fluid dispersing gun 128, and a drainage port 130, connected to a collection bag 132 via a flexible conduit 134.

It is contemplated that medicaments may be included within the pressurized fluid projected onto a wound site. Such medicaments may include clotting factor material such as topical thrombin utilized to treat burns and the like which would be directed towards such wound site either in a pulse or a steady irrigation treatment.

In yet a further embodiment contemplated by the present invention, such an envelope with a securement collar therearound may be utilized for bathing animals or for the treatment of animals (not shown) or patients with a particular skin problem. The access port may be utilized to deliver under pressure a fluid cleaning and hot or cool air at a pressure above atmospheric, to maintain the bag away from the body within the envelope, and that envelope may have one or more drainage ports at its lowermost portion and a feed port for supply of hot or warm air from a blower or dryer to dry off the patient and to heat or cool it. The envelope may have a gas release valve 150, as shown in FIG. 4, to permit varying the temperature of said wound treatment gas supplied to said envelope to permit change and control of the temperature of the wound site of said patient within said envelope, and/or to permit the envelope to be held away from the patient's skin, or to permit the envelope to be utilized as a pressure treatment device as well, to minimize bleeding, to encourage healing and/or medicament application and transfer, or to assist patient treatment. The valve 150 may also comprise a pressure gage to permit the operator of the apparatus to regulate the amount of pressure being applied to the patient's wound site within the envelope. The fluid applying gun 24 or 107 having pressurized gas supply conduit through its housing and discharge nozzle, may be control the gas pressure within the envelope, in conjunction with the operator monitoring the pressure gage 150, which gage 150 has gas release valve capabilities.

The flexible, transparent, manipulable, reinforced, plastic envelopes of the present invention therefore permits a hand held pressurized gas and/or liquid distribution gun to be utilized as a single use apparatus, thus avoiding contamination and handling problems, which is associated with the prior art. The envelopes are readily conformably securable to a limb, and/or around a wound site, to permit a pulse or a constant flow of fluid and/or vapor/gas treatment and tissue debridement under any, condition at almost any location and importantly, from any direction, where such treatment is desirable. The single use envelopes contain waste, and permits a positive pressure within the envelope during the treatment process, to minimize contamination coming into the envelope during that treatment process. By virtue of a further constant pressure pump, fixedly maintained in fluid communication with the envelope, pressure treatment of a wound site can be maintained, while the wound site is maintained sterile and free of contact with the envelope or other irritants which may hinder rapid healing of the wound site of the patient. A vacuum or suction pump or valved drain conduit attached to the collection line/bag, operating at a lower pressure than any pressure infeed, facilitates removal and safe containment of tissue/medicaments, providing safe operating conditions to medical or lay personnel, as well as convenience of such tasks in a manner not shown or taught by the prior art.

I claim:

1. A method of treating a body wound on a patient, comprising the steps of:

applying a flexible transparent envelope about the wound site of the patient being treated, said envelope having at least one primary opening with a peripheral lip to permit said attachment;

introducing a movable hand manipulable fluid applying tissue treatment gun into said envelope;

spraying a fluid into said envelope from said hand manipulable gun, against said wound site, for the treatment of the patient;

spacing said envelope from said wound site by the introduction of a pressurized wound treatment gas into said envelope, whereby said pressurized wound treatment gas is under pressure within said envelope during extended periods of treatment and periods of absence of fluid treatment, to prevent said envelope from contacting said wound site and to maintain the sterility of said wound site;

connecting a discharge port to said envelope to permit drainage of gas and/or fluid from said envelope attached to the patient; and varying the temperature of said wound treatment gas supplied to said envelope to permit change and control of the temperature of the wound site of said patient within said envelope.

2. A method of treating a body wound on a patient, comprising the steps of:

applying a flexible transparent envelope about the wound site of the patient being treated, said envelope having at least one primary opening with a peripheral lip to permit said attachment;

introducing a movable hand manipulable fluid applying tissue treatment gun into said envelope;

spraying a fluid into said envelope from said hand manipulable gun, against said wound site, for the treatment of the patient;

spacing said envelope from said wound site by the introduction of a pressurized wound treatment gas into said envelope, whereby said pressurized wound treatment gas is under pressure within said envelope during extended periods of treatment and periods of absence of fluid treatment, to prevent said envelope from contacting said wound site and to maintain the sterility of said wound site;

connecting a discharge port to said envelope to permit drainage of gas and/or fluid from said envelope attached to the patient; and introducing a clotting factor to said fluid sprayed onto the wound site in said envelope.

* * * * *